United States Patent
Falk et al.

[11] Patent Number: 5,948,999
[45] Date of Patent: Sep. 7, 1999

[54] MOLTEN METAL DIP SAMPLER

[75] Inventors: Richard A Falk, Hillsboro Beach, Fla.;
Michael J Pinterics, Mukwonago, Wis.

[73] Assignee: Midwest Instrument Co., Inc.,
Hartland, Wis.

[21] Appl. No.: 09/022,058

[22] Filed: Feb. 11, 1998

[51] Int. Cl.[6] .................................................. G01N 1/12
[52] U.S. Cl. .................................. 73/864.51; 73/864.55;
73/864.59; 73/DIG. 9
[58] Field of Search ........................... 73/864.51, 864.53,
73/864.55, 864.56, 864.59, DIG. 9

[56] References Cited

U.S. PATENT DOCUMENTS

| | | |
|---|---|---|
| 4,102,197 | 7/1978 | Bardenheuer et al. ......... 73/DIG. 9 X |
| 4,140,019 | 2/1979 | Falk . |
| 4,535,640 | 8/1985 | Falk . |
| 4,896,549 | 1/1990 | Falk . |
| 4,984,904 | 1/1991 | Nakano et al. . |

FOREIGN PATENT DOCUMENTS

| | | |
|---|---|---|
| 0 095 102 | 5/1983 | European Pat. Off. . |
| 1426205 | 2/1976 | United Kingdom ............... 73/DIG. 9 |

*Primary Examiner*—Daniel S. Larkin
*Attorney, Agent, or Firm*—Ryan, Kromholz & Manion

[57] ABSTRACT

A molten metal sampling device for immersion into and sampling of a molten metal includes a sample chamber defined by a mold body formed of heat resistant materials encased in a sand-resin body. At least one fill tube is interconnected with the sample chamber for introduction of molten metal. An air outlet passage is provided for egress of air from the chamber. An annular sleeve of heat resistant inorganic material surrounds the outlet passage, the sleeve being adapted to receive a support tube for supporting the sampling device during use. An elongated retaining strip, preferably a wire formed of a heat resistant metal, is affixed to the mold body and extends over the sleeve, thereby anchoring the sleeve to the mold body. Preferably, a central portion of the wire is affixed to the mold body and opposite ends extend through the sleeve and over an end of the sleeve. Preferably, a metal clamping bracket is affixed to the mold body and embedded in the sand-resin body with the wire extending around a portion of the bracket.

12 Claims, 2 Drawing Sheets

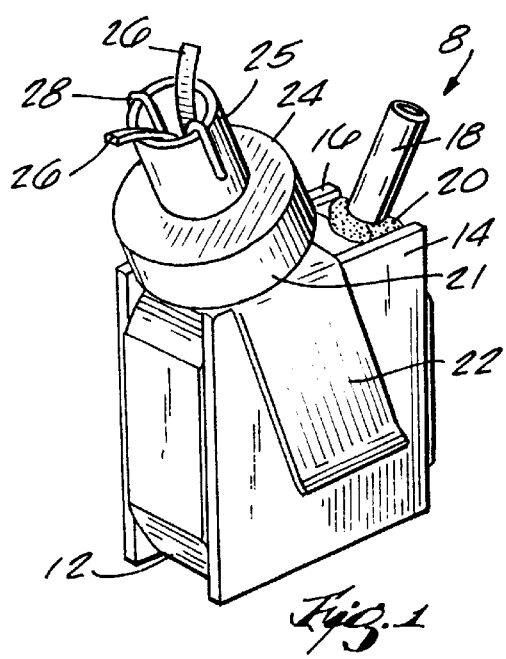
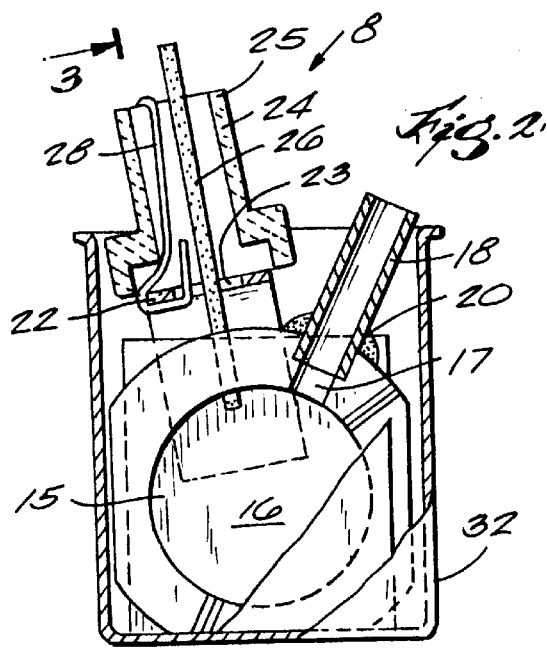
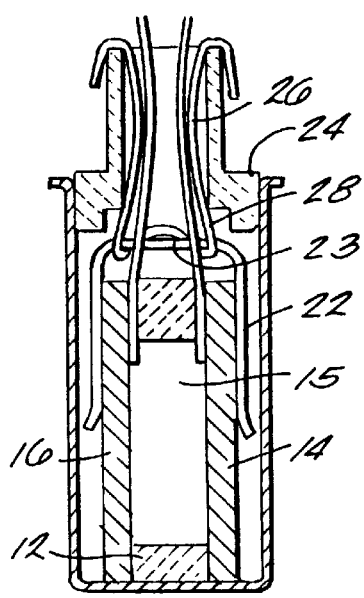
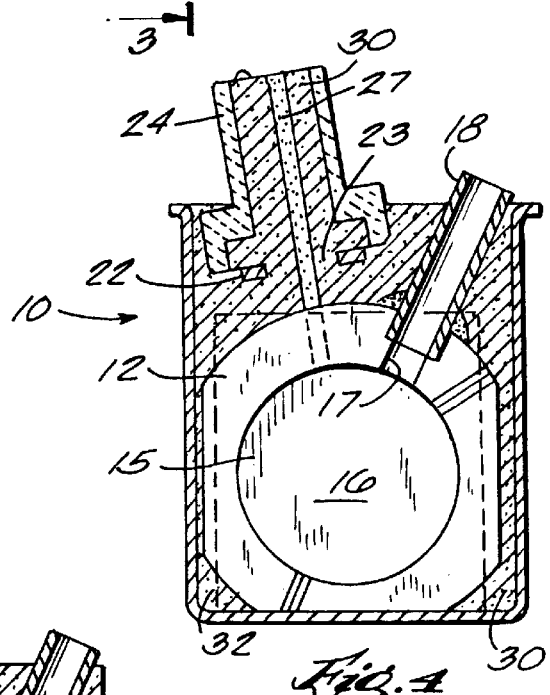
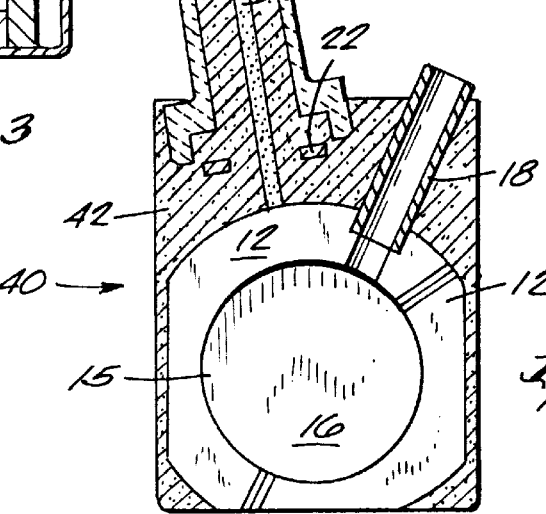

5,948,999

MOLTEN METAL DIP SAMPLER

BACKGROUND OF THE INVENTION

This invention relates to sampling molds for sampling of molten metal by dip immersion of the molds into molten metal baths.

Many prior art devices have been devised for sampling of molten metals. See for example my U.S. Pat. Nos. 3,748, 908; 3,791,219; 4,051,732; 4,069,715; 4,326,426; 4,358, 630; 4,535,640; 4,659,679; and 4,896,549. Also see Wuensch U.S. Pat. No. 4,503,716 or Boron U.S. Pat. No. 4,699, 014.

A number of these known devices utilize a metal sampling chamber which is in many cases embedded in a sand-resin outer layer. Typically, the mold device has a projecting annulus or sleeve which is adapted to receive a tube, such as a cardboard tube, used for supporting the sampling mold during the dipping process. Problems can occur with these molds if the dipping takes place for an excessive period of time due to the fact that the resin portion of the sand resin outer layer can be burned away with the possibility, thus, of disintegration of the mold and resultant contamination of the molten metal bath. This possibility is especially noted in cases where the supporting annulus breaks loose from the rest of the mold. Such breakage may so create a safety hazard for workers in the vicinity of the mold. Because of these problems, the need has existed for improved mold structures.

SUMMARY OF THE INVENTION

It is a principal object of the present invention to provide a sampling mold structure which has improved integrity and resistance to breakage during use.

An important aspect of the present invention is the provision of a reenforcing structure which ties together the components of a dip sampler, while at the same time improving the frictional engagement between the mold and a supporting tube, commonly referred to as a lance tube. A further aspect of the present invention involves providing such a device which avoids contamination of the molten metal or of the retrieved sample. A still further aspect of the invention relates to providing such a device which is cost effective and inexpensive.

Further advantages of the invention relates to the ability to provide dip samplers which are of a non-splash configuration and fast filling at shallow metal immersion depths. An important application relates to molds for obtaining chilled white iron samples. The improved integrity of the molds of this invention is important in achieving these objectives.

Briefly, a molten metal sampling device for immersion into and sampling of a molten metal includes a sample chamber which is defined by a mold body formed of heat resistant materials encased in a sand-resin body. At least one fill tube is interconnected with the sample chamber for introduction of molten metal.

An air outlet passage is provided for egress of air from the chamber. An annular sleeve of heat resistant inorganic material surrounds the outlet passage, the sleeve being adapted to receive a support tube for supporting the sampling device during use. The air passage assists in obtaining of samples which do not contain voids or hollows which might interfere with accurate analysis of the samples. Because the air outlet passage is connected to the interior of the support tube, the mold is efficiently vented by virtue of a riser or "chimney" effect. Shallow immersion of the mold with a desirable quick fill of the mold is thus furthered. Related benefits include obtaining of white iron samples and an avoidance of splashing of molten metal.

A retaining wire or cord or similar elongated strip formed of a heat resistant material, such as a flexible glass fiber cord or metal wire (and preferably having a melting point at least as high as that of the metal to be sampled), is embedded in the sand resin body and extends over the sleeve, thereby anchoring the sleeve to the mold body. Preferably, a central portion of the wire is affixed to the mold body and opposite ends extend through the sleeve and over an end of the sleeve. Preferably, a metal clamping bracket is affixed to the mold body and embedded in the sand-resin body with the wire extending around a portion of the metal bracket.

The sleeve with wires extended thereover enables the use of various inexpensive supporting tubes, for example, those commonly used in shipment of thermocouples, which are generally otherwise discarded. Such tubes have imprecise internal diameters, a dimensional tolerance for the use of the same is provided for by this invention. The wires extending over the sleeve engaged by the supporting tube enables firm frictional engagement by the supporting tube even though the interior diameter might otherwise be too large in relation to the sleeve.

In addition to a cardboard support tube, it will be apparent that other support tubes, such as metal pipes or ceramic-coated tubes can be used, as well. The latter are frequently used in situations where it is desired to reduce smoldering or combustion of cardboard.

Further economies are achieved by virtue of the fact that since the molds can be shipped without accompanying support tubes, shipments are compact and reduced in cost.

Various details of the invention will be set forth with greater clarity in the following detailed description, the claims, and the accompanying drawings.

BRIEF DESCRIPTION OF DRAWINGS

FIG. 1 is a perspective view of a partially assembled sampling device of this invention during the manufacture thereof;

FIG. 2 is a central cross-sectional side view of the device of FIG. 1 with hidden parts shown by phantom lines;

FIG. 3 is a sectional view taken along line 3—3 of FIG. 2;

FIG. 4 is a central cross-sectional side elevational view of a completed sampling device of this invention;

FIG. 5 is a central sectional view showing a further embodiment of the invention.

DETAILED DESCRIPTION OF THE INVENTION

Figure 6:
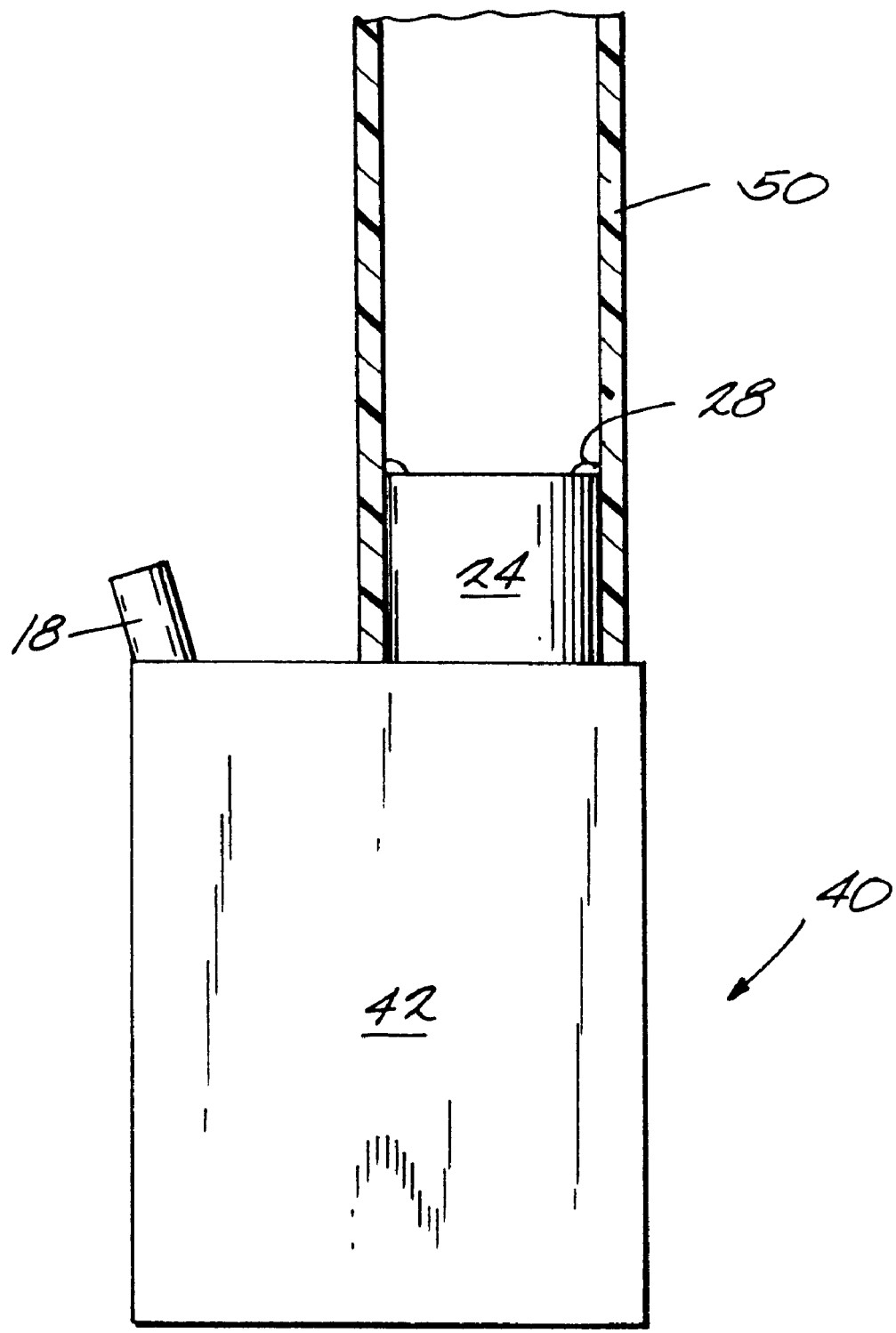
FIG. 6 is a central view of the invention showing the sampler engaged with a supporting tube.

Referring more particularly to FIG. 1 there is shown a partially assembled sampling device 8 in accordance with the invention. Sampling device 8 includes a generally annular ring 12 which forms the body of the device. As best seen in FIGS. 2–4 a hollow inner portion 15 of body 12 forms a sampling chamber. Chill plates 14 and 16 close the otherwise open opposite ends of sample chamber 15.

A fill tube 18 is cemented into an opening 17 through body 12. Refractory cement 20 is preferably used for this purpose. Hollow body portion 12 is preferably formed of a fired ceramic material. Fill tube 18 is preferably formed from a metal such as steel. Chill plates 14 and 16 are also usually formed of steel, as is known in the art.

A U-shaped metal clamping bracket 22 is used to hold the chill plates 14 and 16 against the opposite sides of hollow body 12. Clamping bracket 22 has a central opening 23 through its upper side 21. A ceramic ferrule 24 is connected to the upper end of sampling device 8. Ferrule 24 has an outer diameter at its outwardly and upwardly extending end 25 equal to the inner diameter of a supporting cardboard tube of a type generally used in the art. A pair of combustible strips 26 are positioned through the inside of ferrule 24 and through opening 23 into the mold cavity 15. Upon subsequent firing of device 8, the combustion of strips 26 leave voids which serve to form an air escape route of the mold chamber 15.

As shown, a length of wire 28 is bent around clamping bracket 22 and through the opening 23 therethrough. As best seen in FIG. 1 the opposite ends of wire 28 are then bent downwardly over the outside of ferrule 24. Wire 28 performs a dual purpose, the primary purpose being to secure ferrule 24 to the structure of sampling device 8 thereby overcoming the above noted separation or disintegration problem. A secondary result is that the ends of wires 28 extending over the outside of ferrule 24 serve to frictionally anchor ferrule 24 to a supporting cardboard tube 50 in superior fashion as shown in FIG. 6.

Sampling device 8 is then completed by placing a metal cup structure 32 around the other components of the sampler. A sand-resin mixture 30 is packed around the sampler structure and contained in cup 32. The sand-resin mixture 30 is cured by heating to a range of approximately 400–500° F. to harden the sand-resin mixture. The wire 28 and clamping bracket 22 both remain embedded in the cured sand-resin mixture 30. Simultaneously, the combustible foam or paper strip 26 is vaporized to form the air escape channel 27. Thus, when the completed sampler 10 is utilized, molten metal flows into chamber 15 through fill tube 18. The inflow of the molten metal is facilitated by escape of air through opening 27.

In the alternative embodiment of the invention shown in FIG. 5, a sampler 40 is formed using many of the same components as shown in the case of sampler 10. In this case, similar parts are given the same identifying numerals. Sampler 40, however, involves omission of an outer metallic cup such as cup 32. Instead, the sand-resin mixture 42 forms an integral body of material surrounding the sampler.

From the foregoing it will be appreciated that the improved sampler of this invention has substantially greater integrity than devices provided by the prior art. It will also apparent to those skilled in the art that various modifications of the sampler of this invention can be made free of the invention is thus limited by the scope of the claims including equivalents thereof.

What is claimed is:

1. A molten metal sampling device for immersion into a molten metal for withdrawing a sample therefrom comprising:

a sample chamber defined by a mold body formed of heat resistant materials and encased in a sand-resin body, at least one fill opening interconnected with said sample chamber for introduction therein of molten metal, an air outlet passage for allowing egress of air from said chamber, an annular sleeve of heat resistant inorganic material surrounding said outlet passage, said sleeve adapted to receive a support tube for supporting said sampling device during use, and an elongated retaining strip formed of a heat resistant material embedded in said sand-resin mold body, said strip extending over said sleeve, thereby anchoring said sleeve to said mold body.

2. A device according to claim 1 wherein a central portion of said strip is embedded in said mold body and opposite ends thereof extend through said sleeve and over an end thereof.

3. A device according to claim 2 further comprising a metal clamping bracket affixed to said mold body and embedded in said sand-resin body, said wire extending around a portion of said bracket.

4. A device according to claim 2 wherein said sleeve is adapted to be supported by said support tube, said support tube comprising a cardboard sleeve frictionally fit over said elongated strip.

5. A device according to claim 1 wherein said sand-resin body is encased by a metallic container.

6. A device according to claim 1 wherein said air outlet passage extends from said mold chamber through said annular sleeve whereby air is vented from said mold through the interior of said support tube when fitted over said sleeve.

7. A device according to claim 1 wherein a fill tube is fitted in said fill opening.

8. A molten metal sampling device for immersion into a molten metal for withdrawing a sample therefrom comprising:

a sample chamber defined by a mold body formed of heat resistant materials and encased in a sand-resin body, at least one fill opening interconnected with said sample chamber for introduction therein of molten metal, a fill tube being cemented into said opening, an annular sleeve of heat resistant inorganic material surrounding an outlet passage, said sleeve adapted to receive a support tube for supporting said sampling device during use, said air outlet passage allowing egress of air from said chamber through said annular sleeve and to the atmosphere through the interior of said support tube received over said annular sleeve and, a retaining wire formed of a heat resistant metal, said wire being embedded in said sand-resin body and thereby affixed to said mold body, said wire extending over said sleeve, thereby anchoring said sleeve to said mold body.

9. A device according to claim 8 wherein a central portion of said wire is embedded in said sand-resin body and opposite ends thereof extend through said sleeve and over an end thereof.

10. A device according to claim 9 wherein said sleeve is adapted to be supported by support tubes formed of metal, ceramic-coated metal, or cardboard having variable inner diameters.

11. A device according to claim 8 further comprising a metal clamping bracket affixed to said mold body and embedded in said sand-resin body, said wire extending around a portion of said bracket.

12. A device according to claim 8 wherein said sand-resin body is encased by a metallic container.

\* \* \* \* \*